United States Patent [19]

Blumenthal et al.

[11] Patent Number: 4,967,752
[45] Date of Patent: Nov. 6, 1990

[54] MULTI-PLANAR SCANNING MECHANISM

[75] Inventors: Rafael Blumenthal, Kiriat Tivon; Postar Arkadi, Kiriat Motzkin; Avinoam Livni, Haifa, all of Israel

[73] Assignee: Elscint Ltd., Haifa, Israel

[21] Appl. No.: 385,366

[22] Filed: Jul. 27, 1989

[30] Foreign Application Priority Data

Aug. 2, 1988 [IL] Israel .......................................... 87316

[51] Int. Cl.$^5$ .............................................. A61B 8/12
[52] U.S. Cl. ............................... 128/660.1; 128/662.06
[58] Field of Search ........... 128/660.09, 660.1, 662.06; 73/629, 633

[56] References Cited

U.S. PATENT DOCUMENTS

| 4,543,960 | 10/1985 | Harui et al. | 128/662.06 |
| 4,637,256 | 1/1987 | Sugiyama et al. | 128/660.09 X |
| 4,756,313 | 7/1988 | Terwilliger | 128/662.06 X |
| 4,785,819 | 11/1988 | Pearce | 128/660.1 |

Primary Examiner—Francis Jaworski
Attorney, Agent, or Firm—Sandler, Greenblum & Bernstein

[57] ABSTRACT

A multi-planar scanning endocavital probe for ultrasonic imaging systems including an ultrasonic transducer coupled by a linkage to a selectively rotated motor shaft extending from the face of a motor. The linkage causes the transducer to scan a planar sector wherein the planar sector has a fixed relationship to the motor face. The motor face is moved to change the plane scanned by the transducer.

11 Claims, 3 Drawing Sheets

MULTI-PLANAR SCANNING MECHANISM

FIELD OF THE INVENTION

This invention is concerned with probes for use with ultrasonic imaging systems and more particularly for endocavital probes.

BACKGROUND OF THE INVENTION

The use of ultrasound to obtain images for diagnostic puposes of the interior scanned sectors of patients has been steadily becoming more sophisticated. One of the improvements to ultrasonic diagnostic imaging has been brought about by the use of probes that are inserted into cavities in the body to obtain images of various parts that are juxtaposed to or located within such cavities. Such probes, for example vaginal probes, are severely limited physically by the human body so that, for practical purposes, the probe can only be moved by rotating it around its longitudinal axis. This severely limits the orientation of the scanned sectors.

Therefore, within the spatial limitations of the probe itself, those skilled in the art have been attempting to increase the orientations of the scanned sectors or views that can be obtained by movement of the transducer within the probe. It is relatively simple to place the transducer in such a probe and obtain scans of a single plane or even a few planes. However, it is difficult to design such a probe wherein the transducer will be able to scan a multiplicity of planes that are selected by the operator in an effective manner providing control and repeatability.

In general, the ultrasonic imaging systems comprise a console and a multiplicity of probes individually dedicated to the various specific diagnostic tasks. Probes are plugged interchangeably into a socket or sockets on the console for use in transmitting ultrasonic signals and receiving echoes of these ultrasonic signals. The echoes are sent back to the console for data processing to obtain images from the echoes. The probes detect data used for the reconstruction of the image of a section or a region in the patient's body. The probes include a transducer that converts electrical energy into ultrasound energy and the echoes of the ultrasound energy back into electrical energy.

In general the transducers oscillate (or reciprocate about a fixed axis stationary in the probe. The angle of the scan or of the reciprocating motion is about 110 degrees. That is, a scan sector of 110 degrees is the normal fan shaped field of view in ultrasonic examination. With hand held probes, the probe is brought into contact with the part of the body closest to the region of interest. The plane of the sector is selected by the position of the hand held probe.

More recently, the demand for improved quality images of the organs located inside the body, away from the surface or being in the position where there are acoustically interfering sections of the body, has brought about the utilization of what are herein referred to as endocavital probes. Such probes are inserted into an interior cavity of the body and obtain the data directly from the interior cavity of the body.

The end of the probe usually has a bulbous section which contains the transducer and enables reciprocating motion of the transducer. The end of the bulbous section also contains a viewing window through which the ultrasonic signals and echoes are transmitted and received.

The bulbous section is mounted on an elongated stem which connects a handle to the bulbous section. The handle, in a preferred embodiment, houses the drive motor and control elements. Due to the natural size constraints of the body it is necessary to miniaturize the endocavital parts of the probe. For example, the bulbous section and the stem must be kept radially as small as possible.

Notice that the selection of the sector scanned by the transducer of the probe in the externally applied probes is not limited; whereas in the endocavital probe the sector selected is severely limited and in fact it can be varied only by the rotation of the probe about the stem axis. Thus in the prior art endocavital probes the scan of a sector is accomplished when the transducer reciprocates and to scan additional sectors, the stem is rotated.

In effect, then, there are two types of volumes that are readily obtainable with the presently available endocavital probes. They are a cone shaped volume and a ring shaped volume of revolution. When the center line of the sector scanned by the transducer coincides with the stem axis then rotation of the probe about the stem axis will result in obtaining a cone shaped volume. When the axis of the scanned sector is at right angles to the axis of the stem, then rotation of the probe will result in a ring shaped volume.

To effectively use endocavital probes, it is necessary that they are capable of scanning in more than two planes. Thus, for example, besides locating an organ in the endocavital region, it is helpful for diagnostic purposes, to be able to determine the volume of the organ. This requires scanning in more than one plane and it further requires that the planes that are scanned are not necessarily at right angles to each other but at a multitude of angles to each other between 0 and 90 degrees.

Thus, those skilled in the art are looking for effective methods of obtaining multi-planar images using endocavital probes.

BRIEF DESCRIPTION OF THE INVENTION

In accordance with a broad aspect of the present invention, a multi-planar scanning endocavital probe for an ultrasonic diagnostic imaging system is provided, said probe comprising:

an ultrasonic transducer for converting ultrasonic echo signals into electrical signals, motor means for reciprocatingly rotating a motor shaft extending normally from a face of said motor, linkage means coupling said transducer to said motor shaft to rotate said transducer and cause said transducer to scan a sector in a plane, said scanning plane being fixedly related to the plane of said motor face, and means for pivoting said motor to change the plane in which the transducer scans.

According to a feature of the invention the means for pivoting said motor enables selectively pivoting the motor any amount between at least 0 and 90 degrees.

According to a further feature of the invention, the linkage means comprises a linkage shaft which is coaxial with the shaft of the motor and the linkage shaft is coupled to the motor shaft so that rotation of the motor shaft causes the transducer to rotate with the motor shaft.

A parallelogram arrangement maintains the transducer positioned to scan in a sector that is parallel to the face of the motor. Thereby changing the orientation of the motor changes the plane that is scanned by the transducer.

The arrangement for maintaining the plane of the scan sector in fixed relationship to the face of the motor includes in one preferred embodiment, a pair of parallelograms.

In a second preferred embodiment a single parallelogram is attached to the shaft of the motor through trunions mounted to a yoke shaft arrangement. A lever mounted through the trunions connects the linkage shaft and a push rod to the transducer for orienting the transducer to maintain the scan sector parallel to the face of the motor.

In yet another embodiment of the present invention, the motor shaft is fixed. A meshing bevel gear is mounted to a trunion yoke axially with the trunions. By rotating an adjusting knob the assembly is turned without affecting the relative position of the two gears. The advantage of this version is that the ratio between the gears can be made to increase the sector angle beyond the limits of the motor oscillation.

BRIEF DESCRIPTION OF THE DRAWING

The above mentioned and other features and objects of the present invention will be best understood when considered in the light of the following description of preferred embodiments of the present invention made in conjunction with the accompanying drawings; wherein.

GENERAL DESCRIPTION

Figure 1:
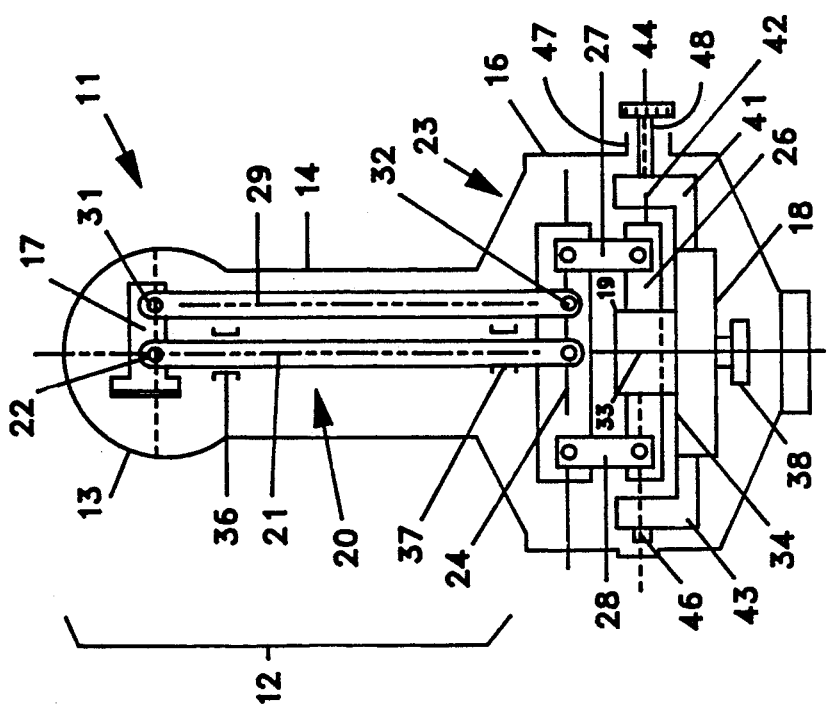
FIG. 1 is a sectional view of a preferred embodiment of an endocavital probe.

FIG. 1 at 11 schematically shows a probe which comprises an envelope 12. The probe is made for insertion into one of the cavities of the patient for viewing the interior of the cavity or for viewing the organs within the cavity or organs positioned close to the cavity.

The envelope 12 comprises a bulb 13 at the end of the envelope. The bulb is attached to a stem section 14. The stem 14 is shown as extending integrally into a handle section 16. The handle section 16 is preferrably maintained exterior to the cavity into which the probe is inserted.

The bulb 13 contains the transducer shown at 17. In the transmitting mode, electrical energy is fed into the transducer 17 through electrical conductor means, not shown, and the transducer converts the electrical signals received from a signal generator, for example, into ultrasonic signals.

The ultrasonic signals are transmitted into the body of the patient and ultrasonic echoes are returned to the transducer from organs within the cavity. The transducer converts the echo signals into electrical signals. The electrical signals are processed and an image is provided.

The handle means 16 contains the motor 18. The motor preferably is a type that moves in a reciprocating motion so that the shaft of the motor 19 rotates backwards and forwards over a preferred number of degrees. In a one embodiment the angle covered by the reciprocating motor is 110 degrees.

The transducer is coupled to the shaft of the motor through linkage means. The linkage in one embodiment comprises a pair of parallelograms. A first parallelogram 20 is comprised of a linkage shaft 21. One end of shaft 21 is connected at point 22 to the transducer. The linkage shaft 21 is connected at its other end to a second parallelogram 23. The second parallelogram comprises a lever 24 and an axle 26 connected together by links 27 and 28. The first parallelogram further includes a push rod 29 connected by pin 31 to the transducer. The push rod is connected to the lever 24 at its other end by pin 32.

The second parallelogram is attached to the shaft 19 of the motor 18 by providing for the axle 26 to pass through a bore 33 in the shaft 19. Thus, the connection between the second parallelogram and the shaft enables a motor to be pivoted around the axle 26.

With the parts of the probe 11 arranged as shown in FIG. 1, the reciprocating rotation of shaft 19 causes the transducer 17 to scan a sector perpendicular to the plane of the paper; that is, parallel to the face 34 of the motor 18. The first parallelogram is made up of the transducer 17 having an axis parallel to the axis of lever 24 and shaft 21 parallel to the push rod 29. The parallelogram parts are interconnected by pins such as pins 22, 31 and 32 previously discussed to enable the ready rotation of the parts of the parallelogram responsive to the rotation of the motor shaft 19. The second parallelogram is made up of the lever 24, parallel to axle 26 and the links 27 and 28 parallel to each other. The parts of the second parallelogram are also shown interconnected by pins. It should be realized that the illustrations of the probe in the Figures is in schematic form and many details are not shown. Bearing means are used wherever necessary even though all the bearings are not shown. Certain bearings are indicated for example, the linkage shaft 21 moves in bearings 36 near the transducer and bearings 37 near the motor shaft.

Means are provided for encoding the position of the motor shaft. More particularly, an encoding wheel 38 is shown coupled to the shaft 19 to indicate the rotational location of shaft 19.

The means for pivoting the motor 18 includes a yoke and trunion arrangement 41 which comprises the trunions 42 and 43. The trunions 42 and 43 are aligned with the axis of axle 26. The motor pivots around the axle 26 responsive to the operation of means such as handle 44. The handle 44 is fixedly connected to the trunion 42 portion of the yoke 41. A bearing arrangement 46 is operative at the trunion 43 of yoke 41. A bearing shown for providing bearings for stem 48 of knob 44.

Figure 2:
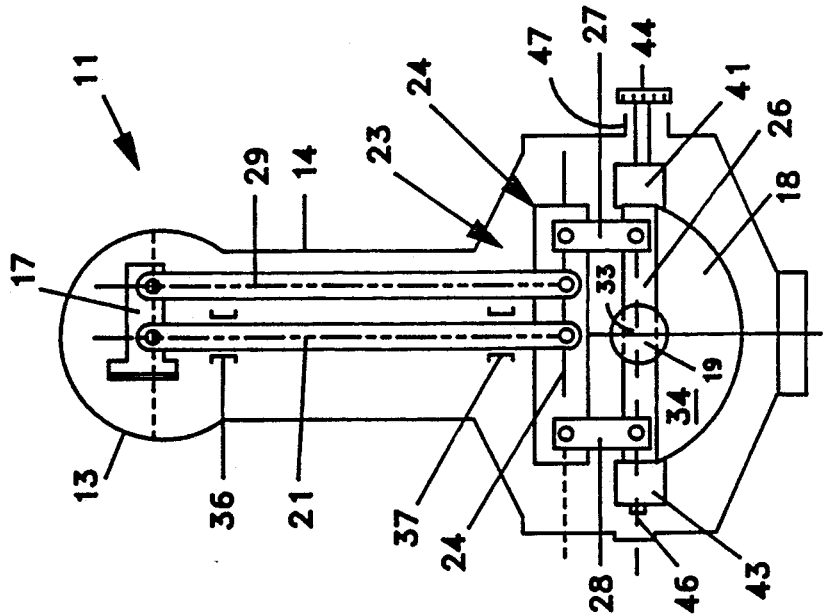
FIG. 2 shows the endocavital probe of FIG. 1 with the motor pivoted 90 degrees.

FIG. 2 is a showing of the same probe 11, as shown in FIG. 1. In FIG. 2 however, the motor 18 is pivoted through 90 degrees, using the knob 44. The same reference numbers are used in FIG. 2 as were previously used in FIG. 1. Note that with the motor pivoted as in the arrangement of FIG. 2 the transducer scans a sector in a plane parallel to the plane of the paper of the drawing. The plane of the paper, of course, is parallel to the face 34 of the motor in FIG. 2.

Figure 3:
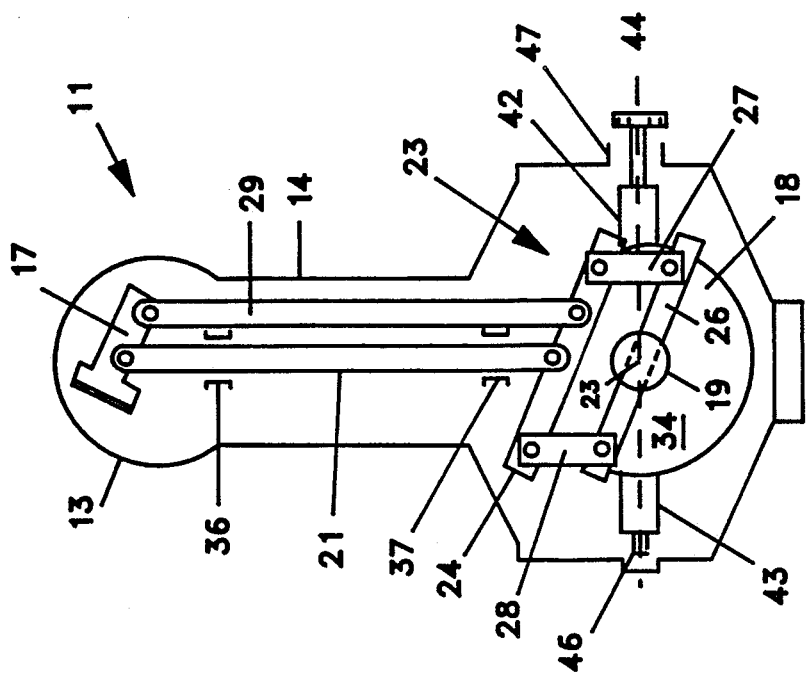
FIG. 3 is a different phase of the scan of FIG. 2 with the motor pivoted 90 degrees.

FIG. 3 shows the probe of FIG. 2 in position when the motor is rotated to it's maximum amount clockwise.

The parallelograms in FIG. 3 both have vertical parts. For example, in the first parallelogram 20 the link shaft 21 and the push rod 29 both remain vertical. However, the transducer 17 is now slanted with the face of the transmitting portion of the transmitter at its highest portion in the scanning arc. The second parallelogram also has vertical members; i.e. lengths 27 and 28 remaining vertical while the previously horizontal members, i.e. the lever 24 and the axle 26 are now slanted responsive to the rotation of motor shaft 19.

Figure 4:
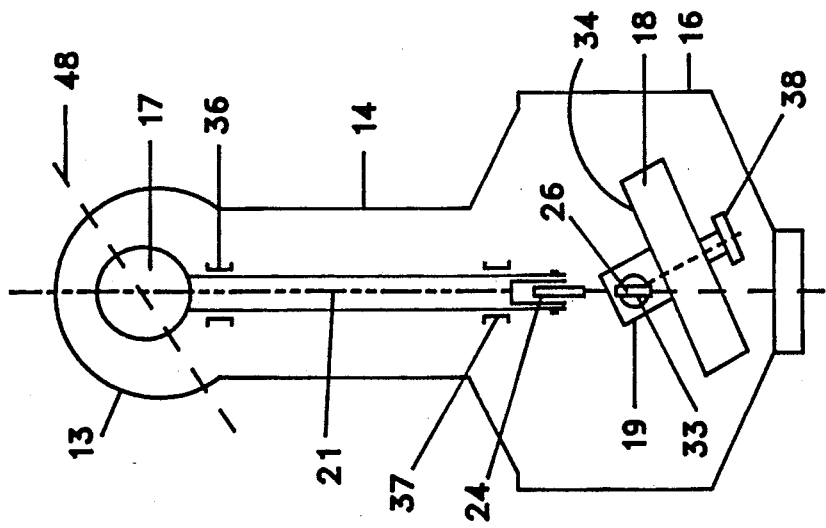
FIG. 4 shows the probe of FIG. 1 with the motor pivoted 45 degrees.

FIG. 4 is illustrative of the versatility of the invention. Therein the motor 18 is shown as being pivoted 45 degrees around the axle 26. The rotation of the motor shaft 19 causes the transducer 17 to define a plane whose side view is line 48. In other words, the plane scanned by transducer 17 remains parallel to the face 34 of motor 18. Thus, FIG. 4 shows that the linkage arrangement comprised of the first parallelogram and the second parallelogram maintains the plane of the scanned sector parallel to the face of the motor. Thus, changing the orientation of the face of the motor, which is readily done using knob 44, changes the plane of the scan sector. Thus, an infinite number of planes can be selected and scanned in accordance with this invention. The selection and control of the plane of the scan sector is accomplished outside of the internal cavity being scanned by using control means such as the control knob 44 for pivoting the motor to change the plane of the sector being scanned.

Figures 5, 6:
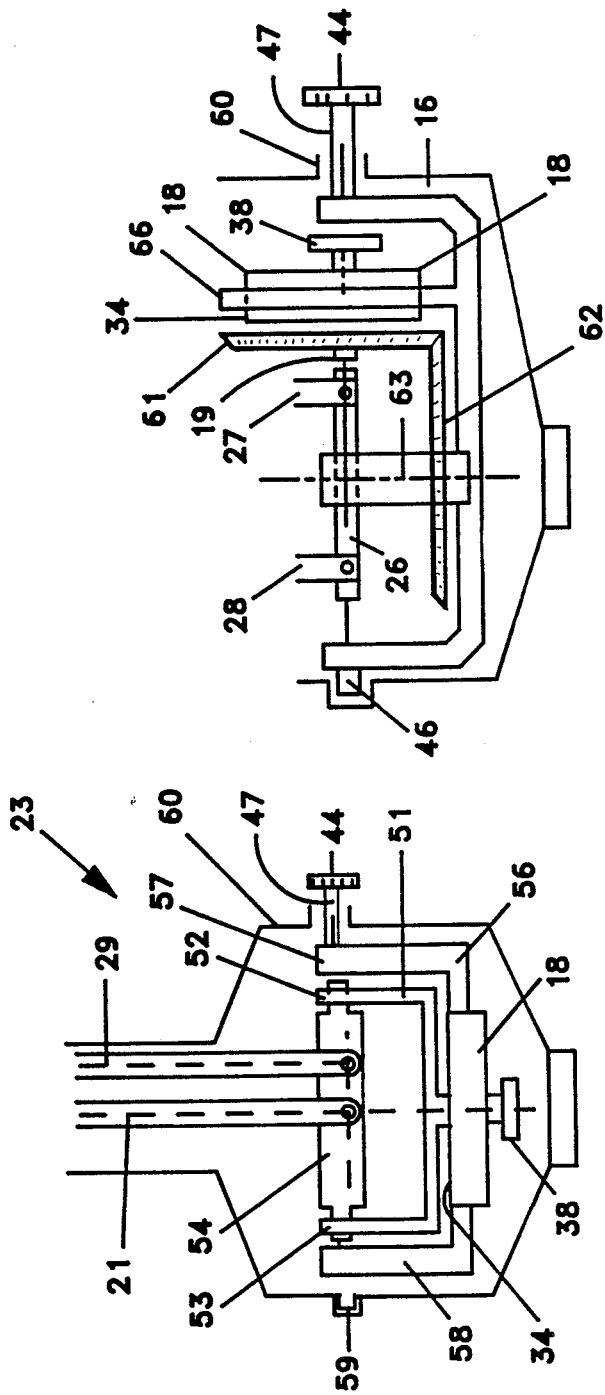
FIG. 5 is part of the probe of FIG. 1 with a different arrangement for connecting the linkage to the motor shaft.
FIG. 6 shows another embodiment of the probe of FIG. 1 with still another arrangement for connecting the shaft to the linkage.

The embodiment of FIG. 5 eliminates the second parallelogram. The first parallelogram remains precisely as shown in FIGS. 1–3. Thus, the linkage shaft 21 is still shown in the exemplary showing of the probe in FIG. 5. In addition, the push rod 29 is still shown. The shaft 21 and push rod 29 are coupled to the transducer (not shown in FIG. 5) in the same manner as the couplings of FIGS. 1–4.

Instead of the second parallelogram a new arrangement is provided. The motor shaft 19 is now replaced by a yoke shaft arrangement 51. The yoke shaft arrangement 51 has the yoke portion ending in trunion sections 52 and 53. The trunion sections 52 and 53 contain a lever 54 similar to lever 24. The similarity includes the connection to lever 54 of the linkage shaft 21 and the push rod 29. The motor 18 also has fixedly connected thereto a second yoke means 56 which terminates in trunions 57 and 58. The trunions 57 and 58 are shown as also being aligned with the axis of lever 54. The trunion 57 fixedly receives the knob stem 47 to which is connected the knob 44. Stem 47 is ridgidly attached to a trunion 57 and is used for pivoting the motor around the axis of lever 54 at trunions 52 and 53. The motor also pivots around the bearing arrangement 59 at trunion 58. Encoding means are shown at 38 to assure proper location of yoke shaft arrangement 51 at all times. Thus, by using the yoke shaft arrangement 51, it is possible to eliminate the second parallelogram.

The embodiment of FIG. 5 emphasizes that a main feature of the invention is not the second parallelogram or the first parallelogram but an arrangement, whereby the scanning sector plane is maintained at fixed relationship to the face 34 of the motor 18. Thus, by selectively pivoting motor 18, it is possible to select the plane that is being scanned by the transducer 17.

In the first embodiment of FIGS. 1–4, note that the lever 24 was not mounted to be rotatable. In the embodiment of FIG. 5 however, lever 54 is mounted so that the motor can pivot thereabout. In the first embodiment, the motor does not pivot around the lever 24 it pivots around the axle 26 of the second parallelogram.

FIG. 6 further illustrates the versatility of the invention. In FIG. 6 a bevel gear 61 is attached to motor shaft 19 whereby the rotation of shaft 19 rotates drive bevel gear 61 which in turn rotates driven bevel gear 62. The rotation of gear 62 rotates shaft 63 fixedly mounted in bevel gear 61. The rotation of shaft 63 in a reciprocating manner, or otherwise, similarly causes rotation of the axle 26 and of course of the lever 24 not shown. This causes the transducer 17 to rotate and scan in a plane perpendicular to the plane of the paper. Other gears enable "amplifying" the angular size of the scan sector without increasing the angle covered by the reciprocating motion of the motor 34.

In the embodiment of FIG. 6, means for retaining the motor 34 is shown as retaining means 66. It should be noted that in the embodiment of FIG. 6 the plane of the scan sector is no longer parallel with the face of the motor 34. In fact it is perpendicular to the face of the motor because of the bevel gear arrangement.

In operation an arrangement for probing and examining endocavities in patients is provided. The probe arrangement includes a bevel arrangement which maintains the relationship between the face of the transducer and the face of the motor so that the scanned sector can be selected by pivoting the motor to change the orientation of the face of the motor. In one preferred embodiment, the scanned sector is always parallel to the face of the motor. In another preferred embodiment the scanned sector is normal to the face of the motor. One embodiment utilizes linkage means between the motor and the transducer that comprises a pair of interacting parallelograms. In another embodiment a parallelogram and a shaft-yoke arrangement are used to link the same motor and the transducer. In any case, the orientation of the plane of the scan sector is determined by the orientation of the motor. The determination of the sector orientation is an analog type of orientation and thus, the scan sector can be in an infinate number of planes at the choice of the operator. The arrangement is easy to control and repeatable so that an infinite variety of scan sector planes can be selected with the inventive arrangement.

While the invention has been described with relation to some preferred embodiments, it should be noted that the description is made by way of example, only and not any limitations on the scope of the invention which invention is more specifically determined by the accompanying claims.

What is claimed is:

1. A multi-planar scanning endocavital probe for ultrasonic diagnostic imaging systems, said probe compring:

a housing containing an ultrasonic transducer for converting electrical signals to ultrasonic signals and for converting ultrasonic echo signals back to electrical signals, motor means in said housing for reciprocatingly rotating a motor shaft, said shaft extending from a face of said motor, linkage means coupling said transducer to said motor shaft to cause said transducer to reciprocate in a plane to thereby provide a scan said plane being at a fixed relationship to said motor face, and means for pivoting said motor means with respect to said housing to adjust said motor means to move said motor face to change the plane in which said transducer scans with respect to said housing to enable scanning over a selected one of a multiplicity of planes.

2. The multi-planar scanning endocavital probe of claim 1 wherein the said plane in which said transducer reciprocates is parallel to said motor face as the fixed relationship of said plane to said motor face.

3. The multi-planar scanning endocavital probe of claim 1 wherein said linkage means coupling said transducer to said motor shaft comprises a first parallelogram coupled to said transducer and coupling means coupling said first parallelogram to said motor means, said first parallelogram comprising:

said first parallelogram defining an axis of said transducer as one side, lever means coupled to said motor shaft being a side of said first parallelogram parallel to said transducer axis, parallelogram shaft means in said first parallelogram coupling said transducer to said lever means, and a push rod in said first parallelogram parallel to said parallelogram shaft means and spaced apart from said first parallelogram shaft means also coupling said transducer to said lever means to complete said first parallelogram.

4. The multi-planar scanning endocavital probe of claim 3 wherein said linkage means comprises a second parallelogram, said second parallelogram comprising said parallelogram lever means of said first parallelogram and axle means parallel to said parallelogram lever means, first and second links spaced apart parallel to each other and attached to said lever means and said axle means to complete said second parallelogram, and said motor shaft being pivotably connected to said axle means.

5. The multi-planar scanning endocavital probe of claim 4 wherein said motor shaft has an aperture therein normal to the axis of said motor shaft for pivotably connecting said motor means to said coupling means.

6. The multi-planar scanning endocavital probe of claim 3 further comprises second linkage means which comprises a pair of bevel gears, a first of said bevel gears being attached to said motor shaft, a second of said bevel gears being at right angles to said first of said bevel gears and meshing with the first of said bevel gears, gear shaft means extending from the second of said bevel gears to said first parallelogram, and means for pivotably coupling said gear shaft to said first parallelogram.

7. The multi-planar scanning endocavital probe of claim 1 wherein said means for pivoting said motor means to change the plane in which said transducer scans comprises trunnion means on which said motor means is pivotable, and knob means coupled to said motor means for pivoting said motor means.

8. The multi-planar scanning endocavital probe of claim 7 wherein said means for pivoting said motor face to change the plane in which said transducer scans further includes:

a motor yoke attached fixedly to the body of said motor means, said trunnion means comprising a pair of trunnions on said motor yoke, and said knob means fixedly attached to a first trunnion of said pair of trunnions.

9. A multi-planar scanning endocavital probe for ultrasonic diagnostic imaging systems, said probe comprising:

an ultrasonic transducer for converting electrical signals to ultrasonic signals and for converting ultrasonic echo signals back to electrical signals.

motor means for reciprocatingly rotating a motor shaft, said shaft extending from a face of said motor, linkage means coupling said transducer to said motor shaft to cause said transducer to reciprocatingly move to scan a sector, said transducer moving in a plane parallel to said motor face, said linkage means comprising a first parallelogram including a longitudinal axis of said transducer and a second parallelogram coupled to said motor shaft, said first parallelogram further comprising:

lever means coupled to said motor shaft parallel to said transducer axis, a parallelogram shaft means coupling said transducer to said lever means, a push rod parallel to said parallelogram shaft means and also coupling said transducer to said lever means to complete the first parallelogram, and knob means for pivoting said motor means to change the plane in which said transducer scans to enable scanning in selected ones of a multiplicity of planes.

10. The multi-planar scanning endocavital probe of claim 9 including shaft yoke arrangement for pivotally linking said motor shaft to said second parallelogram.

11. The multi-planar scanning endocavital probe of claim 9 wherein said means for pivoting said motor means to reorient said motor face to change the plane in which said transducer moves includes encoding means for indicating the position of said motor face.

* * * * *